(12) United States Patent
Wu et al.

(10) Patent No.: US 12,051,204 B2
(45) Date of Patent: Jul. 30, 2024

(54) AUTOMATIC ORGAN GEOMETRY DETERMINATION

(71) Applicant: Shanghai United Imaging Intelligence Co., Ltd., Shanghai (CN)

(72) Inventors: Ziyan Wu, Lexington, MA (US); Srikrishna Karanam, Brighton, MA (US); Meng Zheng, Cambridge, MA (US); Abhishek Sharma, Boston, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 422 days.

(21) Appl. No.: 17/538,232

(22) Filed: Nov. 30, 2021

(65) Prior Publication Data

US 2023/0169657 A1   Jun. 1, 2023

(51) Int. Cl.
*G06N 3/08* (2023.01)
*G06T 7/00* (2017.01)
*G06T 7/50* (2017.01)
*G06T 7/73* (2017.01)
*G16H 30/40* (2018.01)
*G16H 50/50* (2018.01)

(52) U.S. Cl.
CPC ............. *G06T 7/0014* (2013.01); *G06N 3/08* (2013.01); *G06T 7/50* (2017.01); *G06T 7/74* (2017.01); *G16H 30/40* (2018.01); *G16H 50/50* (2018.01); *G06T 2207/10028* (2013.01); *G06T 2207/20081* (2013.01); *G06T 2207/20084* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 7,925,326 B2 | 4/2011 | Siegel et al. | |
| 8,896,679 B2 | 11/2014 | Hyde et al. | |
| 9,044,173 B2 | 6/2015 | Crouch | |
| 9,355,309 B2 | 5/2016 | Tridandapani et al. | |
| 11,282,218 B2 * | 3/2022 | Karanam | G06N 20/00 |

(Continued)

FOREIGN PATENT DOCUMENTS

| | | |
|---|---|---|
| CN | 101987019 A | 3/2011 |
| CN | 111862174 A | 10/2020 |

(Continued)

*Primary Examiner* — Dov Popovici
(74) *Attorney, Agent, or Firm* — Zhong Law LLC

(57) ABSTRACT

The shape and/or location of an organ may change in accordance with changes in the body shape and/or pose of a patient. Described herein are systems, methods, and instrumentalities for automatically determining, using an artificial neural network (ANN), the shape and/or location of the organ based on human models that reflect the body shape and/or pose the patient. The ANN may be trained to learn the spatial relationship between the organ and the body shape or pose of the patient. Then, at an inference time, the ANN may be used to determine the relationship based on a first patient model and a first representation (e.g., a point cloud) of the organ so that given a second patient model thereafter, the ANN may automatically determine the shape and/or location of the organ corresponding to the body shape or pose of the patient indicated by the second patient model.

20 Claims, 6 Drawing Sheets

(56) References Cited

U.S. PATENT DOCUMENTS

| | | | |
|---|---|---|---|
| 2014/0090173 A1 | 4/2014 | DiMaio et al. | |
| 2014/0357984 A1 | 12/2014 | Wallace et al. | |
| 2021/0158937 A1* | 5/2021 | Wu | G06V 10/7796 |
| 2021/0358595 A1* | 11/2021 | Tamersoy | G06T 7/33 |

FOREIGN PATENT DOCUMENTS

| | | |
|---|---|---|
| CN | 111862175 A | 10/2020 |
| CN | 112232362 A | 1/2021 |
| EP | 3754666 A1 | 12/2020 |
| JP | 5186269 B2 | 4/2013 |

\* cited by examiner

AUTOMATIC ORGAN GEOMETRY DETERMINATION

BACKGROUND

Organ shape and location determination is an important aspect of clinical applications. Pre-operative planning and radiation therapy, for example, require precise knowledge of the physical characteristics of a target organ such as its orientation, contours, volume, etc. Modern medical imaging technologies provide means for obtaining such knowledge. But since the physical characteristics of an organ may change in accordance with the body shape and/or pose of the patient, a medical scan image of the organ acquired at a previous time (e.g., pre-treatment) may not reflect the characteristics of the organ at a present time (e.g., during treatment). As a result, patients are often required to maintain a same pose or position during different medical procedures. When that is not possible, additional imaging may be needed to account for changes in the patients' body shapes and/or poses. The dependency of organ shape and/or organ location on a patient's body shape and/or pose may also pose challenges for conducting comparative studies of the organ. For example, since the medical scan images of an organ taken at different times may be inherently different in accordance with the body shape and/or pose of the patient, it may be difficult to isolate pathological changes of the organ from non-pathological changes that are caused by variations in the patient's body shape and/or pose.

Accordingly, systems and methods for automatically determining the shape and/or location of an organ based on the body shape and/or pose of a patient may be highly desirable. These systems and methods may be used, for example, to facilitate treatment and pre-operative planning, improve the precision and effectiveness of surgical operations, avoid or reduce unnecessary medical scans, lower the radiation exposure of patients, enable comparative clinical studies and/or diagnosis, etc.

SUMMARY

Described herein are systems, methods, and instrumentalities for automatically determining the geometric characteristics of an organ based on the body shape and/or pose of a patient. An apparatus configured to perform this task may comprise one or more processors configured to receive a first model of the patient and a representation of the organ. The first model may indicate a body shape or pose of the patient while the representation of the organ may indicate a geometric characteristic (e.g., shape and/or location) of the organ corresponding to the body shape or pose indicated by the first model. Based on the model and the representation of the organ, the one or more processors of the apparatus may be configured to determine, using an artificial neural network (ANN), a relationship between the geometric characteristic of the organ and the body shape or pose of the patient. Such a relationship may be represented, for example, by a plurality of parameters indicating the spatial relationship between one or more points of the organ and one or more points of the first model. Upon determining the relationship, the one or more processors of the apparatus may receive a second model of the patient indicating that at least one of the body shape or pose of the patient has changed from the body shape or pose indicated by the first model. The one or more processors may determine, based on the second model and the determined relationship between the organ and the body shape or pose of the patient, the geometric characteristic of the organ corresponding to the body shape or pose of the patient indicated by the second model.

The ANN described herein may be trained to learn the relationship between the geometric characteristic (e.g., shape and/or location) of the organ and the body shape or pose of the patient based on a plurality of patient training models and a plurality of training representations of the organ. As described above, such a relationship may be reflected through a plurality of parameters that the ANN may learn during the training. An example training process of the ANN may include one or more of the following steps. For each of the plurality of patient training models, the ANN may obtain, from the plurality of training representations, a representation of the organ that corresponding to the body shape and/or pose of the patient represented by the patient training model. The ANN may estimate values of the plurality of parameters described above based on the training model and the representation of the organ. The ANN may then obtain a second training model of the patient and generate an estimated representation of the organ based on the estimated values of the plurality of parameters and the second training model. The ANN may then compare the estimated representation it has generated with a training representation (e.g., as a ground truth representation) of the organ that corresponds to the second patient model, and adjust the operating parameters (e.g., weights) of the ANN based on a difference (e.g., a gradient descent associated with the difference) between the ground truth representation and the representation predicted by the ANN.

In examples, the ANN described herein may include one or more encoders and one or more decoders. The one or more encoders may be trained to determine the relationship (e.g., the plurality of parameters that reflects the relationship) between the geometric characteristic of the organ and the body shape or pose of the patient based on a first model of the patient and a first representation of the organ. The one or more decoders may be trained to construct, based on a second model of the patient and the relationship determined by the encoder, a representation of the organ corresponding to the body shape or the pose of the patient indicated by the second model.

In examples, each of the representations of the organ described herein may comprise a point cloud (e.g., three-dimensional point cloud) that may be obtained based on at least a scan image of the organ taken when the patient is in the body shape or pose indicated by a corresponding patient model. In examples, such a point cloud may be obtained by aligning the scan image of the organ with the corresponding patient model and determining the point cloud based on the alignment. In examples, each of the patient models described herein may comprise a respective parametric model of the patient, and the patient models may be generated based on respective images of the patient captured by one or more sensing devices. In examples, the apparatus described herein may include the one or more sensing devices.

The techniques described herein for automatically determining the geometric characteristic of an organ based on the body shape and/or pose of the patient may be used to serve multiple clinical purposes. For example, upon determining the geometric characteristic of the organ corresponding to a second patient model (e.g., indicating a second body shape or pose of the patient), a scan image taken when the patient is in a first body shape or pose (e.g., indicated by a first patient model) may be manipulated to be aligned with the second patient model. This may not only eliminate the need for additional scans of the organ, but also allow diagnostic studies and treatment planning to be conducted in accordance with changes in the body shape and/or pose of the patient.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings.

Figure 1:
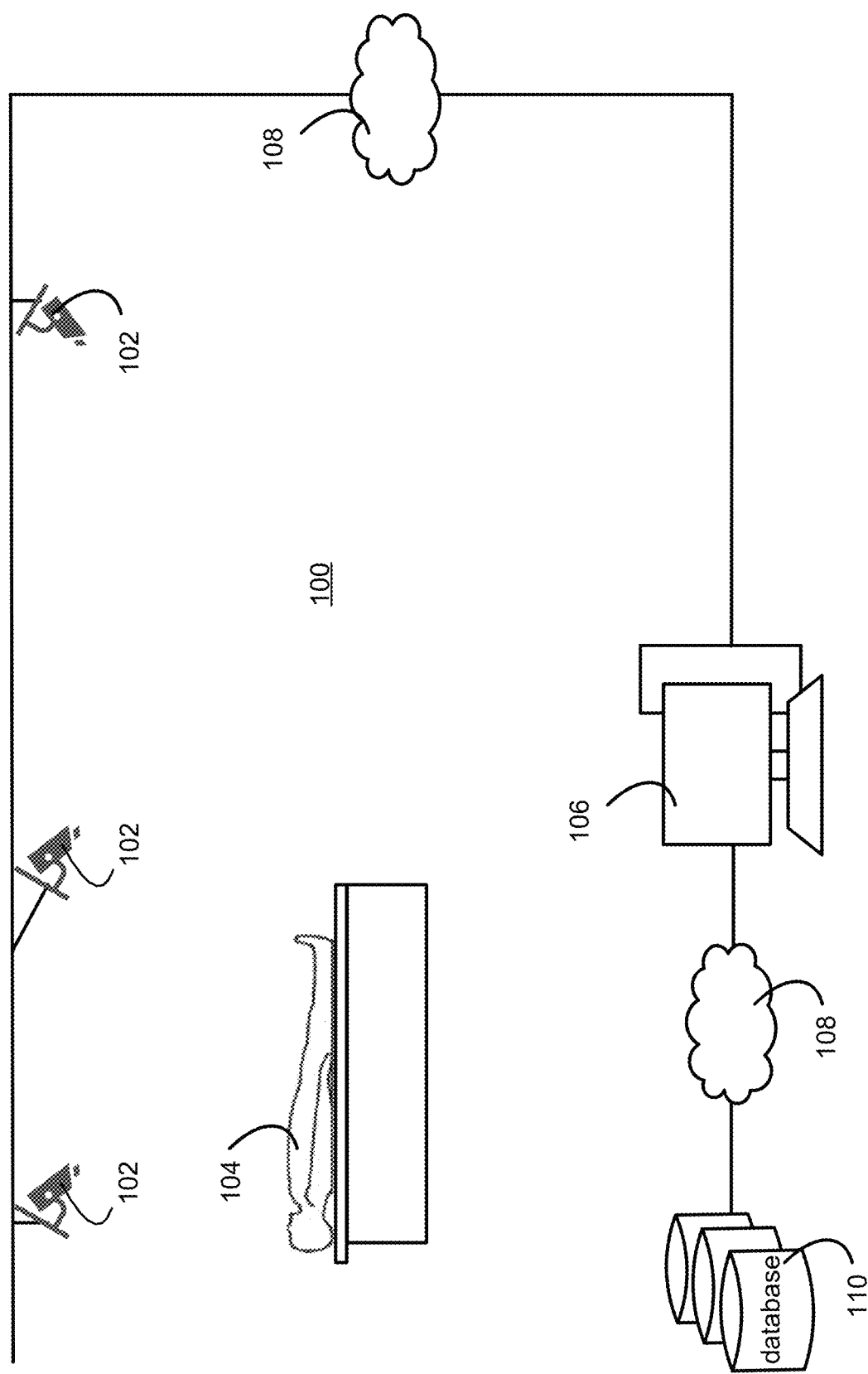
FIG. 1 is a simplified diagram illustrating an example environment associated with one or more of the embodiments described herein.

FIG. 1 is a simplified diagram illustrating an example environment 100 associated with one or more of the embodiments described herein. Environment 100 may be part of a medical facility such as a scan room (e.g., magnetic resonance imaging (MRI), X-ray, Computed Tomography (CT), etc.) or an operating room (OR), a rehabilitation facility, a fitness center, etc. Environment 100 may be equipped with one or more sensing devices (e.g., 102a, 102b, 102c) such as one or more digital cameras configured to capture images (e.g., two-dimensional (2D) images) of patient 104 inside the environment 100. Sensing devices 102a-c may be communicatively coupled to processing device 106 and/or other devices of environment 100 via communication network 108. Each of sensing devices 102a-c may include one or more sensors such as one or more 2D visual sensors (e.g., 2D cameras), one or more 3D visual sensors (e.g., 3D cameras), one or more red, green, and blue (RGB) sensors, one or more depth sensors, one or more RGB plus depth (RGB-D) sensors, one or more thermal sensors (e.g., infrared (FIR) or near-infrared (NIR) sensors), one or more radar sensors, and/or other types of image capturing devices or circuitries.

Each of sensing devices 102a-c may include a functional unit (e.g., a processor) configured to process the images captured by the sensing device and/or to generate (e.g., construct) a human model such as a 3D human mesh model of the patient based on the images. Such a human model may include a plurality of parameters that indicates the body shape and/or pose of the patient while the patient is inside environment 100 (e.g., during an MRI, X-ray, or CT procedure). For example, the parameters may include shape parameters β and pose parameters θ that may be used to determine multiple vertices (e.g., 6890 vertices based on 82 shape and pose parameters) associated with the patient's body and construct a visual representation of the patient model (e.g., a 3D mesh), for example, by connecting the vertices with edges to form polygons (e.g., such as a triangles), connecting multiple polygons to form a surface, using multiple surfaces to determine a 3D shape, and applying texture and/or shading to the surfaces and/or shapes.

The patient model described above may also be generated by processing unit 106. For example, processing unit 106 may be communicatively coupled to one or more of sensing devices 102a-c and may be configured to receive images of the patient from those sensing devices (e.g., in real time or based on a predetermined schedule). Using the received images, processing unit 106 may construct the patient model, for example, in a similar manner as described above. It should be noted here that, even though processing unit 106 is shown in FIG. 1 as being separate from sensing devices 102a-c, any one of sensing devices 102a-c may be configured to operate as processing unit 106 (e.g., using one or more functional units or processors included in the sensing device). For example, sensing devices 102a-c may be interconnected via communication link 108 and exchange images with each other. One of the sensing devices may be configured to perform the model construction tasks described herein based on images received from the other sensing device(s).

Sensing device 102a-c or processing unit 106 may be further configured to automatically determine the geometric characteristics of an organ of the patient based on the body shape and/or pose the patient indicated by the patient model described above. The organ may be, for example, the spleen, liver, heart, etc. of the patient and the geometric characteristics may include, for example, the shape and/or location of the organ that corresponds to the body shape and/or pose of the patient indicated by the patient model. In examples, sensing device 102a-c or processing unit 106 may be configured to automatically determine these geometric characteristics of the organ using a machine-learned model that may indicate a correlation (e.g., a spatial relationship) between the geometric characteristics of the organ and the body shape and/or pose of the patient. In examples, such a machine-learned model may take a patient model and a representation (e.g., a three-dimensional (3D) point cloud) of the organ as inputs and produce an output (e.g., a plurality of parameters) that indicates how the geometry (e.g., shape and/or location) of the organ may change in accordance with changes in the patient's body shape and/or pose. As such, using the machine-learned model, sensing device 102a-c or processing unit 106 may determine the correlation between the geometric characteristics of the organ and the body shape and/or pose of the patient based on a first patient model and a first representation of the organ, and upon obtaining a second patient model indicating that the body shape and/or pose of the patient has changed, automatically determine the geometric characteristics of the organ that correspond to the body shape and/or pose indicated by the second patient model.

The techniques described herein may serve a variety of purposes. For example, based on automatically determined shape and/or location of an organ that correspond to a second patient model (e.g., which may indicate a second body shape and/or second pose of the patient), a scan image of the organ associated with a first patient model (e.g., which may indicate a first body shape and/or first pose of the patient) may be manipulated to align with the second patient model. The aligned scan image and patient model may then be used to determine changes in the structural and/or functional state of the organ independent of potential changes in the body shape and/or pose of the patient and without additional scans of the organ. Having the ability to automatically determine the geometry (e.g., shape and/or location) of the organ corresponding to the second body shape and/or pose of the patient may also allow medical procedures (e.g., surgeries, radiation therapies, etc.) planned based on the first body shape and/or pose to be adapted to accommodate the changes in the patient's body shape and/or pose.

Information regarding the automatically determined geometry (e.g., shape and/or location) of the organ and/or the patient models described herein may be provided in real time to a downstream application or device (e.g., such as a surgical robot). The information may also be saved (e.g., as metadata associated with a scan image) to a repository (e.g., database 110 shown in FIG. 1), which may be communicatively coupled to sensing devices 102a-c and/or processing unit 106 to receive the information. Such metadata may be used subsequently to align the medical scan(s) associated with the metadata with other models of the patient (e.g., if the patient's body shape and/or pose changes in those models) or with other medical scans of the patient (e.g., such as those captured by a different image modality).

The patient models described herein may be derived independently of each other (e.g., based on different images of the patient taken at different times throughout a year) or one patient model may be derived based on another patient model and/or a given protocol (e.g., such a protocol may indicate that a second patient model may share the same characteristics of a first patient model except for the pose of the patient). In examples, medical scans of a patient that correspond to different patient models (e.g., different body shapes and/or poses at different times) may be aligned to determine changes in an organ of the patient. For instance, the patient may undergo multiple scan procedures throughout a year and during/after every scan procedure the scan image may be linked to a parametric model (e.g., 3D mesh) representing the body shape and/or pose of the patient during the scan procedure. Subsequently, by manipulating the respective shape and/or pose parameters of the parametric models, the models obtained during different scan procedures may be updated to reflect a same body shape and/or pose of the patient such that the scan images may also be aligned to a same body shape and/or pose of the patient. This way, the scan images (e.g., segmentations masks associated with the scan images) may be compared and evaluated to determine how an organ of the patient may have evolved over time.

In examples, a first patient model may be generated based on a position of the patient in a scan room and a second patient model may be generated based on a position of the patient in a surgery room (e.g., based on data acquired by a sensing device in the surgery room). By aligning scan images that are associated with the first patient model with the second patient model (e.g., based on automatically determined organ shape and/or location corresponding to the second patient model), the aligned scan images may be used for surgery planning, surgery guidance, or patient diagnosis. In examples, given a treatment, surgery, or procedure plan devised based on a first patient model, a second patient model and/or an automatically determined organ shape and/or location may be used to correct, update, or renew the plan. In examples, the patient models and/or an automatically determined organ shape and/or location may be used to optimize scanning parameters to target a treatment area, adjust radiation dosage, etc. In examples, a patient model may be generated based on information (e.g., images of the patient) captured at an injured scene. By aligning medical scans of the patient with such a patient model, more accurate assessment of the injury may be accomplished.

Figure 2:
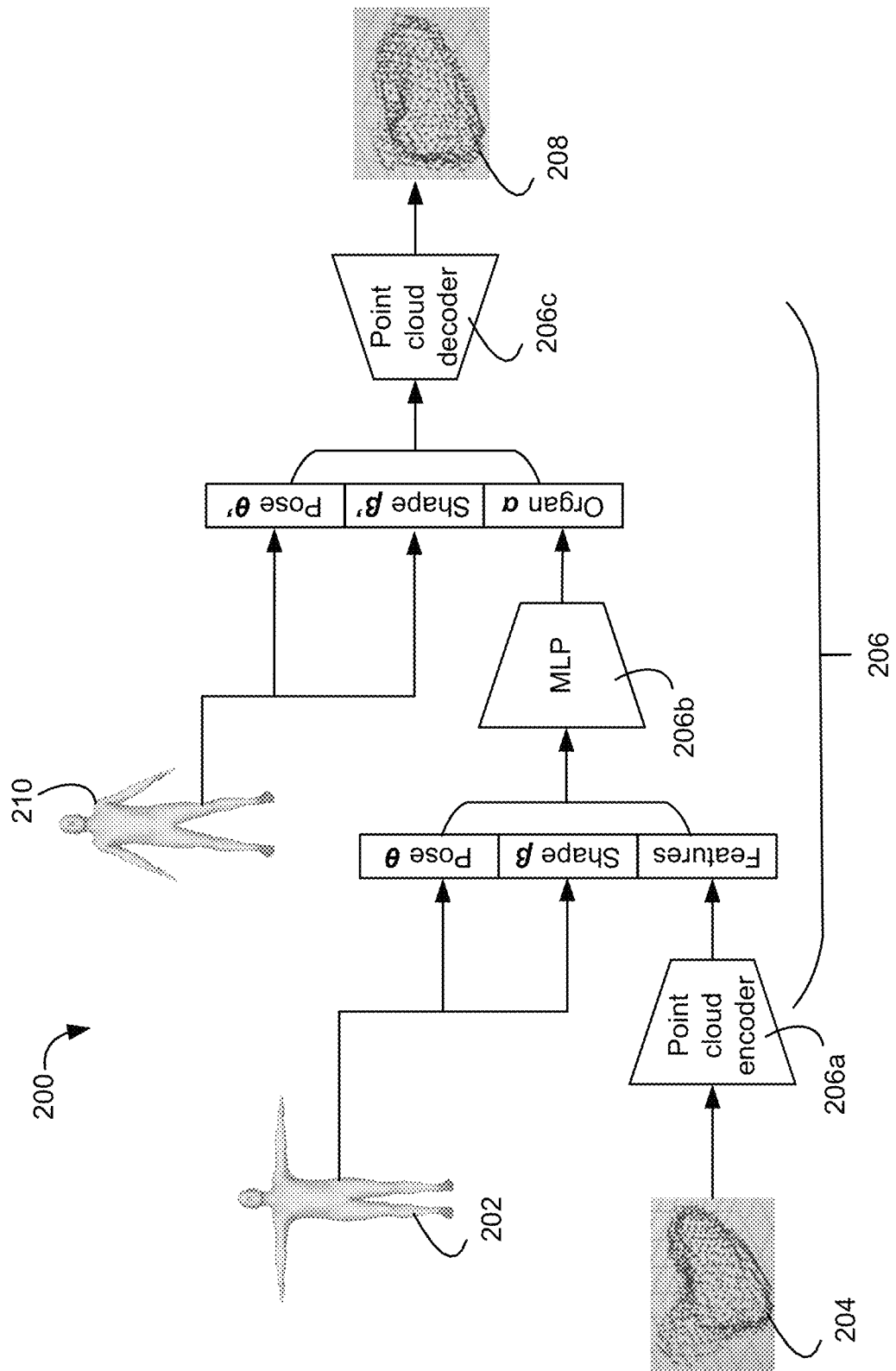
FIG. 2 is a simplified diagram illustrating example operations associated with the automatic determination of an organ shape and/or an organ location in accordance with one or more embodiments described herein.

FIG. 2 is a simplified diagram illustrating example operations that may be performed to automatically determine the geometric characteristics of an organ. These example operations may be performed by a device or apparatus such as processing unit 106 or sensing device 102a, 102b, or 102c shown in FIG. 1. For ease of description, such a device or apparatus may be referred to herein as an organ geometry estimator. As shown by FIG. 2, organ geometry estimator 200 may be configured to obtain first model 202 of a patient and representation 204 of an organ (e.g., spleen, live, heart, etc.) of the patient. First model 202 may include a parametric model of the patient, a two-dimensional (2D) or three-dimensional (3D) contour of the patient, a 3D mesh of the patient, a 3D point cloud representing the body shape and/or pose of the patient, a 2D or 3D skeletal representation of the patient, a descriptor of one or more 2D or 3D joint locations of the patient, a set of measurements indicating the physical characteristics of the patient, and/or other types of representations that may indicate the body shape and/or pose of the patient when the patient is in a certain position (e.g., standing in front of a scanning device, lying on a surgery bed, etc.). Using parametric models as an example, first model 202 may include a plurality of parameters such as a plurality of pose parameters θ (e.g., 72 pose parameters associated with the joints of the patient) and/or a plurality of shape parameters β (e.g., 10 coefficients of a principal component analysis (PCA) space) that may be used to determine the body shape and/or pose of the patient (e.g., via a 3D mesh). First model 202 may be generated by organ geometry estimator 200 or a different device or apparatus based on images (e.g., RGB images, depth images, thermal images, etc.) of the patient captured by the sensing devices described herein (e.g., sensing devices 102a-c of FIG. 1). If generated by a device other than organ geometry estimator 200, first model 202 may be provided (e.g., the parameters of first model 202 may be provided) to organ geometry estimator 200 for performing the operations shown in FIG. 2.

Representation 204 shown in FIG. 2 may indicate one or more geometric characteristics (e.g., shape and/or location) of the organ corresponding to the body shape and/or pose of the patient represented by first model 202. Representation 204 may be obtained in various forms including, for example, a 3D point cloud of the organ, a parametric model (e.g., a 3D parametric model) of the organ, etc. Representation 204 may be generated, for example, based on one or more scan images of the organ (e.g., taken while the patient is in the body shape and/or pose indicated by the first model 202) and a statistical shape model of the organ. The statistical shape model may include a mean shape of the organ (e.g., a mean point cloud indicating the shape of the organ) and a principal component matrix that may be used to determine the shape of the organ depicted by the one or more scan images (e.g., as a variation of the mean shape) based on features extracted from the one or more scan images. The statistical shape model may be predetermined, for example, based on sample scan images of the organ collected from a certain population or cohort and segmentation masks of the organ corresponding to the sample scan images. The segmentation masks may be registered with each other via affine transformations and the registered segmentation masks may be averaged to determine a mean point cloud representing a mean shape of the organ. Based on the mean point cloud, a respective point cloud may be derived in the image domain for each sample scan image, for example, through inverse deformation and/or transformation. The derived point clouds may then be used to determine a principal component matrix, for example, by extracting the principal modes of variations to the mean shape.

It should be noted that representation 204 (e.g., a point cloud) may be derived by organ geometry estimator 200 or by a different device or apparatus. In the latter case, representation 204 may be provided to organ geometry estimator 200 for performing the example operations described herein. As shown in FIG. 2, organ geometry estimator 200 may include an artificial neural network (ANN) 206 trained to determine the correlation (e.g., a spatial relationship) between the geometric characteristics (e.g., shape and/or location) of the organ and the body shape and/or the pose of a patient based on model 202 of the patient and representation 204 of the organ. Such a correlation may be represented, for example, through a plurality of parameters (e.g., referred to herein as $\alpha$) that may indicate how the geometric characteristics of the organ may change in accordance with changes in the patient's body shape and/or pose (e.g., from a first body shape and/or first pose to a second body shape and/or second pose).

In examples, ANN 206 may include point cloud feature encoder 206a trained to extract features from representation 204 of the organ. Point cloud feature encoder 206a may include a convolutional neural network (CNN) with a plurality of layers such as one or more convolutional layers, one or more pooling layers, and/or one or more fully connected layers. Each of the convolutional layers may include a plurality of convolution kernels or filters configured to extract features from representation 204. The convolution operations may be followed by batch normalization and/or line or non-linear activation, and the features extracted by the convolutional layers may be down-sampled through the pooling layers and/or the fully connected layers (e.g., using a 2×2 window and a stride of 2) to reduce the redundancy and/or dimension of the features (e.g., by a factor of 2) to obtain a representation of the down-sampled features, for example, in the form of a feature map or feature vector (e.g., a PTC or point cloud vector).

In examples, ANN 206 may include encoder 206b trained to encode the features of representation 204 extracted by point cloud feature encoder 206a, the shape parameters $\beta$, and/or the pose parameters $\theta$ into a plurality of parameters $\alpha$ that represents the correlation (e.g., a mapping or spatial relationship) between the geometric characteristics (e.g., shape and/or location) of the organ and the body shape or pose of the patient. In examples, encoder 206b may include a multi-layer perception (MLP) neural network with multiple layers (e.g., an input layer, an output layer, and one or more hidden layers) of linearly or non-linearly-activating nodes (e.g., perceptrons) trained to infer the correlation between the geometric characteristics of the organ and the body shape or pose of the patient and generate parameters $\alpha$ to represent the correlation. In examples, parameters $\alpha$ may include a vector of floating point numbers (e.g., float32 numbers) that may be used to determine the locations (e.g., coordinates) of one or more points on representation 204 (e.g., in the image domain) based on the locations (e.g., coordinates) of one or more points on first model 202 (e.g., in the image domain). Subsequently, given second model 210 of the patient that indicates a new (e.g., different) body shape and/or pose of the patient (e.g., compared to first model 202), organ geometry estimator 200 may generate (e.g., estimate or predict) representation 208 (e.g., a point cloud) based on parameters $\alpha$ to indicate the geometric characteristics (e.g., shape and/or location) of the organ under the new body shape and/or pose indicated by second model 210.

In examples, ANN 206 may include point cloud decoder 206c trained to generate representation 208 (e.g., a point cloud) based on parameters $\alpha$ and model 210 of the patient. In examples, point cloud decoder 206c may include one or more un-pooling layers and one or more transposed convolutional layers. Through the un-pooling layers, point cloud decoder 206c may up-sample the features of point cloud 204 extracted by point cloud encoder 206a and encoded by encoder 206b, and further process the up-sampled features through one or more transposed convolution operations to derive a dense feature map (e.g., up-scaled from the original feature map produced by point cloud encoder 206a by a factor of 2). Based on the dense feature map, point cloud decoder 206c may recover representation 208 of the organ to reflect changes in the geometric characteristics of the organ (e.g., changes in the shape and/or location of the organ) caused by changes in the body shape and/or pose of the patient as indicated by second model 210.

Figure 3:
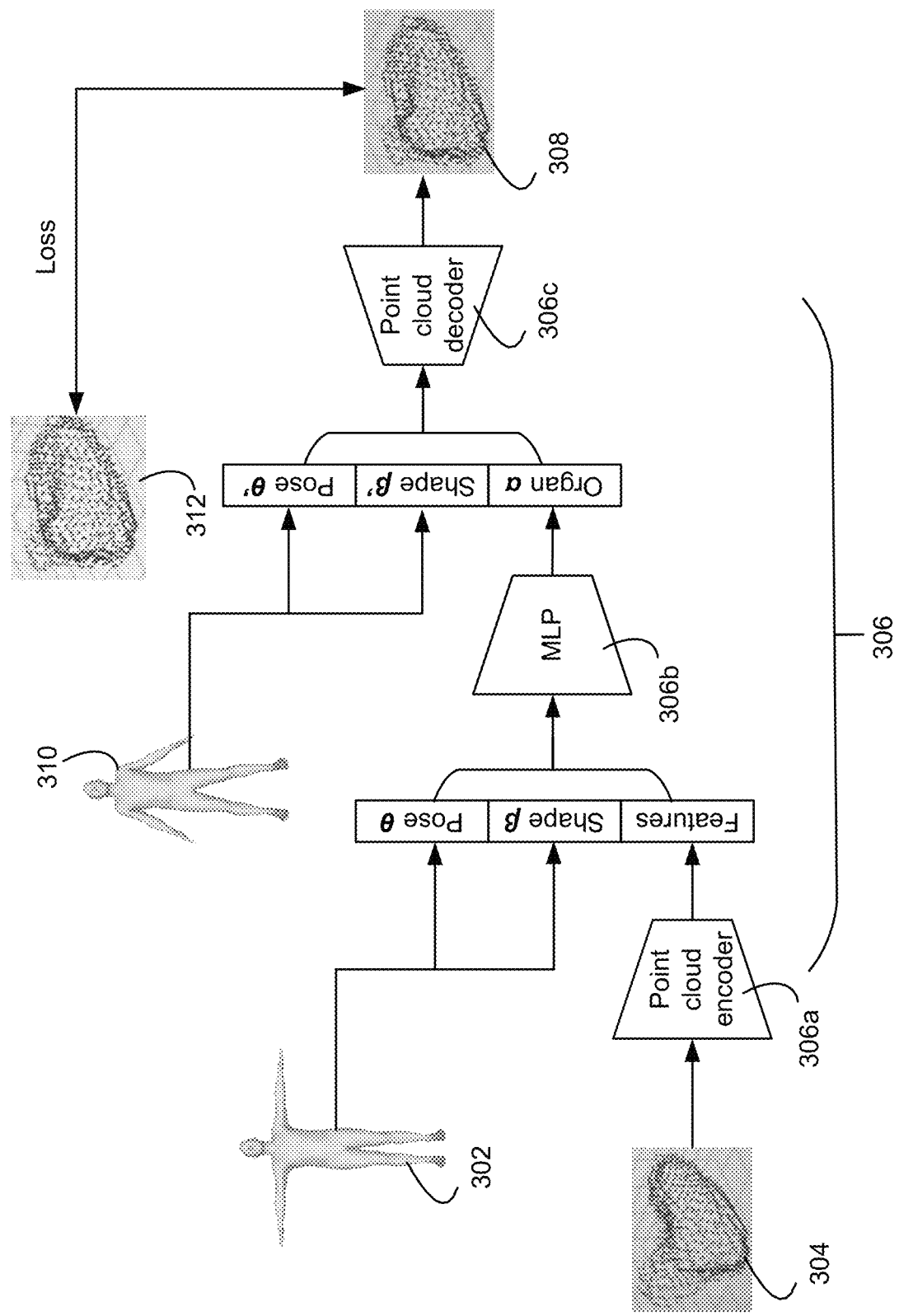
FIG. 3 is a simplified diagram illustrating the training of a neural network in accordance with one or more embodiments described herein.

FIG. 3 is a simplified diagram illustrating an example of training a neural network (e.g., neural network 306, which may be an instance of ANN 206 shown in FIG. 2) for automatically determining the geometric characteristics (e.g., shape and/or location) of an organ based on the body shape and/or pose of a patient. The training may be conducted using a plurality of patient models (e.g., parametric human models such as skinned multi-person linear (SMPL) models) and a plurality of representations (e.g., 3D point clouds) of the organ, which may be obtained from publicly available training datasets. Each of the plurality of representations of the organ may be associated (e.g., paired) with a corresponding one of the plurality of patient models (e.g., the training representation may depict the shape and/or location of the organ when the corresponding patient is in the position indicated by the patient model). As described herein, each of the patient models used for the training may include a plurality of pose parameters $\theta$ (e.g., 72 pose parameters), a plurality of shape parameters $\beta$ (e.g., 10 coefficients of a PCA space), and/or a plurality of vertices (e.g., (6890, 3) vertices) that may be derived based on pose parameters $\theta$ and shape parameters $\beta$. Similarly, each of the representations used for the training may include a plurality of parameters (e.g., (512, 3) vertices of a 3D point cloud) indicating the geometric characteristics (e.g., shape and/or location) of the organ.

During the training process, neural network 306 may obtain first patient training model 302 and corresponding first training representation 304 of the organ. Through point cloud encoder 306a, neural network 306 may extract features from first training representation 304 and provide the extracted features, together with shape parameters $\beta$ and pose parameters $\theta$ of first training model 304, to encoder (e.g., an MLP encoder) 306b to estimate parameters $\alpha$. As described herein, parameters $\alpha$ may represented a correlation or mapping (e.g., a spatial relationship) between the geometric characteristics of the organ (e.g., reflected through representation 304) and the body shape and/or pose of the patient (e.g., reflected through first training model 302) in the image space. Neural network 306 may then obtain second patient training model 310 and a corresponding second training representation 312 of the organ. Using point cloud decoder 306c, neural network 306 may estimate representation 308 (e.g., a point cloud) of the organ based on parameters α predicted by MLP encoder 306b and shape parameters β' and/or pose parameters θ' of second training model 310. Neural network 306 may then compare representation 308 with second training representation 312 (e.g., a ground truth representation) and determine a loss associated with the encoding and/or decoding operations described above. Such a loss may be determined based on various loss functions including, for example, mean squared errors (MSE), an L1 norm, an L2 norm, a structural similarity index (SSIM), etc. Once the loss is determined, neural network 306 may adjust its parameters (e.g., the weights associated with the various filters or kernels of point cloud encoder 306a, MLP encoder 306b, and point cloud decoder 306c) by backpropagating the loss through neural network 306 (e.g., based on a gradient descent of the loss).

Figure 4:
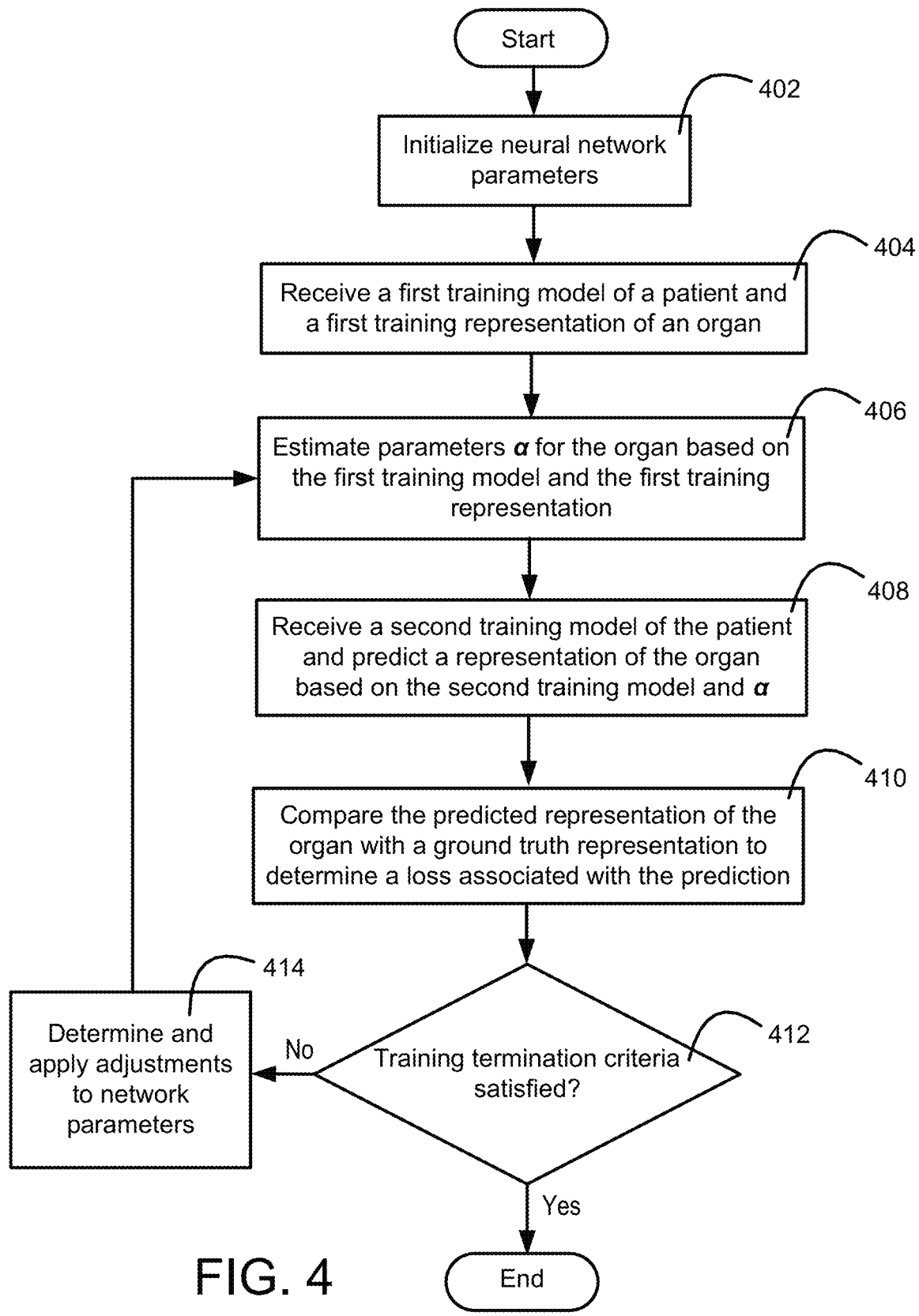
FIG. 4 is a simplified flow diagram illustrating example operations that may be associated with the training of a neural network in accordance with one or more embodiments described herein.

FIG. 4 illustrates example operations that may be performed during the training a neural network (e.g., an instance of ANN 206 shown in FIG. 2) described herein. For example, at 402, parameters of the neural network (e.g., weights associated with various filters or kernels of the neural network) may be initialized. The parameters may be initialized, for example, based on samples collected from one or more probability distributions or parameter values of another neural network having a similar architecture. At 404, the neural network may receive a first training model (e.g., an SMPL model) of a patient and a first training representation (e.g., a 3D point cloud) of an organ (e.g., spleen) of the patient. At 406, the neural network may extract features from the first training representation and estimate the values of a plurality of parameters α based on the extracted features and the parameters of the first training model (e.g., shape parameters β and/or pose parameters θ). As described herein, parameters α may indicate a correlation or mapping (e.g., a spatial relationship) between a body shape and/or pose of the patient and a geometric characteristic (e.g., shape and/or pose) of the organ.

At 408, the neural network may receive a second training model (e.g., an SMPL model) of the patient that may include second shape parameters β' and second pose parameters θ', and the neural network may predict a representation (e.g., a point cloud) of the organ based on the second training model and estimated parameters α. As described herein, such a representation of the organ may depict the geometric characteristic of the organ corresponding to the body shape and/or pose of the patient indicated by the second training model (e.g., by second shape parameters β' and/or second pose parameters θ'). At 410, the neural network may compare the predicted representation of the organ with a ground truth representation (e.g., provided as a part of the training data) to determine a loss associated with the prediction. As described herein, the loss may be determined based on an MSE, an L1 norm, an L2 norm, an SSIM, etc. Once determined, the loss may be used to determine at 412 whether one or more training termination criteria have been satisfied. For example, a training termination criterion may be deemed satisfied if the determined loss is below a predetermined threshold, if a change in the respective losses of two training iterations (e.g., between consecutive training iterations) is below a predetermined threshold, etc. If the determination at 412 is that a training termination criterion has been satisfied, the training may end. Otherwise, the neural network may at 414 adjust its parameters by backpropagating the loss (e.g., based on a gradient descent associated with the loss) through the neural network, before the training returns to 406 at which the neural network may make another prediction for α.

For simplicity of explanation, the training steps are depicted and described herein with a specific order. It should be appreciated, however, that the training operations may occur in various orders, concurrently, and/or with other operations not presented or described herein. Furthermore, it should be noted that not all operations that may be included in the training process are depicted and described herein, and not all illustrated operations are required to be performed.

Figure 5:
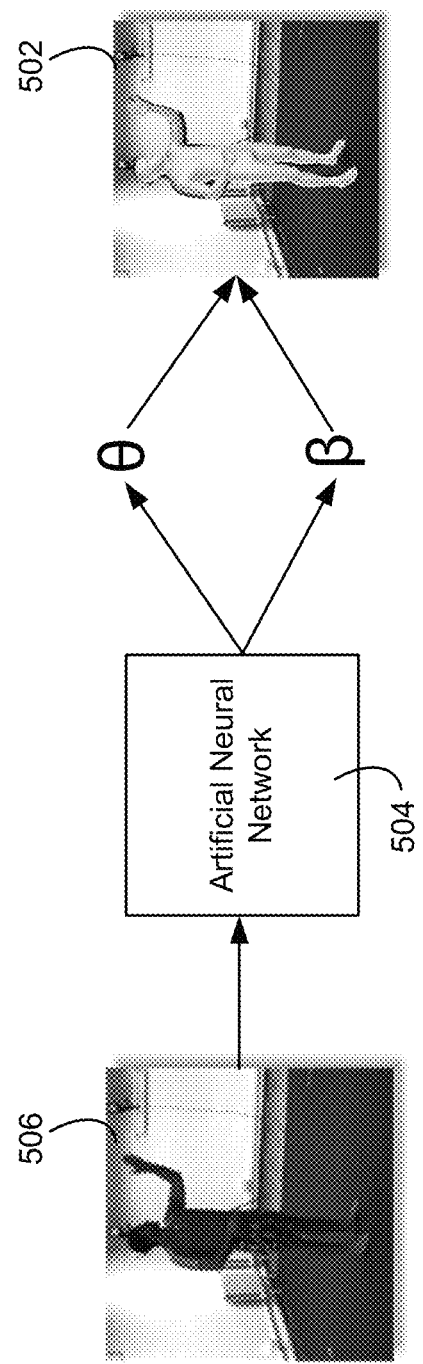
FIG. 5 is a simplified diagram illustrating an example of human mesh recovery in accordance with one or more embodiments described herein.

FIG. 5 shows a simplified block diagram illustrating how patient model 502 (e.g., patient model 202, 210 of FIG. 2 or patient model 302, 310 of FIG. 3) may be recovered using neural network 504 based on image 506 (e.g., a 2D image or 2D+depth image) of the patient. Neural network 504 may be a part of the organ geometry estimator described herein (e.g., a part of ANN 206 shown in FIG. 2). Neural network 504 may also be a separate network trained for recovering patient models. In either case, neural network 504 may comprise multiple layers such as an input layer, one or more convolutional layers, one or more linear or non-linear activation layers, one or more pooling layers, one or more fully connected layers, and/or an output layer. One or more of these layers may include respective filters (e.g., kernels) each of which may be designed to detect (e.g., learn) keypoints that collectively represent a feature or a pattern. The filters may be associated with respective weights that, when applied to an input, produce an output indicating whether certain features or patterns have been detected. The weights associated with the filters may be learned by the neural network through a training process that comprises inputting a large number of images from one or more training datasets to the neural network, predicting an output (e.g., a set of features identified in each of the input training images), calculating a difference or loss resulting from the prediction (e.g., based on a loss function such as an MSE, an L1 norm, etc.), and updating the weights assigned to the various filters (e.g., based on a stochastic gradient descent of the loss) to minimize the loss. Once trained (e.g., having learned to extract features from the training images), the neural network may take an image at the input layer, extract and/or classify features or patterns from the image, and provide an indication at the output layer regarding the identified features. The identified feature may be indicated, for example, with a feature map or a feature vector.

Neural network 504 may also be trained to infer, e.g., based on features extracted from input image 506, pose parameters θ and shape parameters β that may be used to recover patient model 502. For example, neural network 504 may be trained to determine, based training datasets that cover a wide range of human subjects, human activities, background noises, shape and/or pose variations, camera motions, etc., the joint angles of the patient as depicted in input image 506. The joint angles may be associated with, for example, 23 joints comprised in a skeletal rig as well as a root joint, and the pose parameters θ derived thereof may include 72 parameters (e.g., 3 parameters for each of the 23 joints and 3 parameters for the root joint, with each parameter corresponding to an axis-angle rotation from a root orientation). Neural network 504 may be trained to determine shape parameters β for predicting a blend shape of the patient person based on image 506. For example, neural network 504 may learn to determine shape parameters β through PCA and the shape parameters thus determined may include a plurality of coefficients (e.g., the first 10 coefficients) of the PCA space. Once the pose and shape parameters are determined, a plurality of vertices (e.g., 6890 vertices based on 82 shape and pose parameters) may be obtained for constructing a visual representation (e.g., a 3D mesh) of the patient's body. Each of the vertices may include respective position, normal, texture, and/or shading information. Using these vertices, a 3D mesh of the patient may be created, for example, by connecting multiple vertices with edges to form a polygon (e.g., such as a triangle), connecting multiple polygons to form a surface, using multiple surfaces to determine a 3D shape, and applying texture and/or shading to the surfaces and/or shapes.

Figure 6:
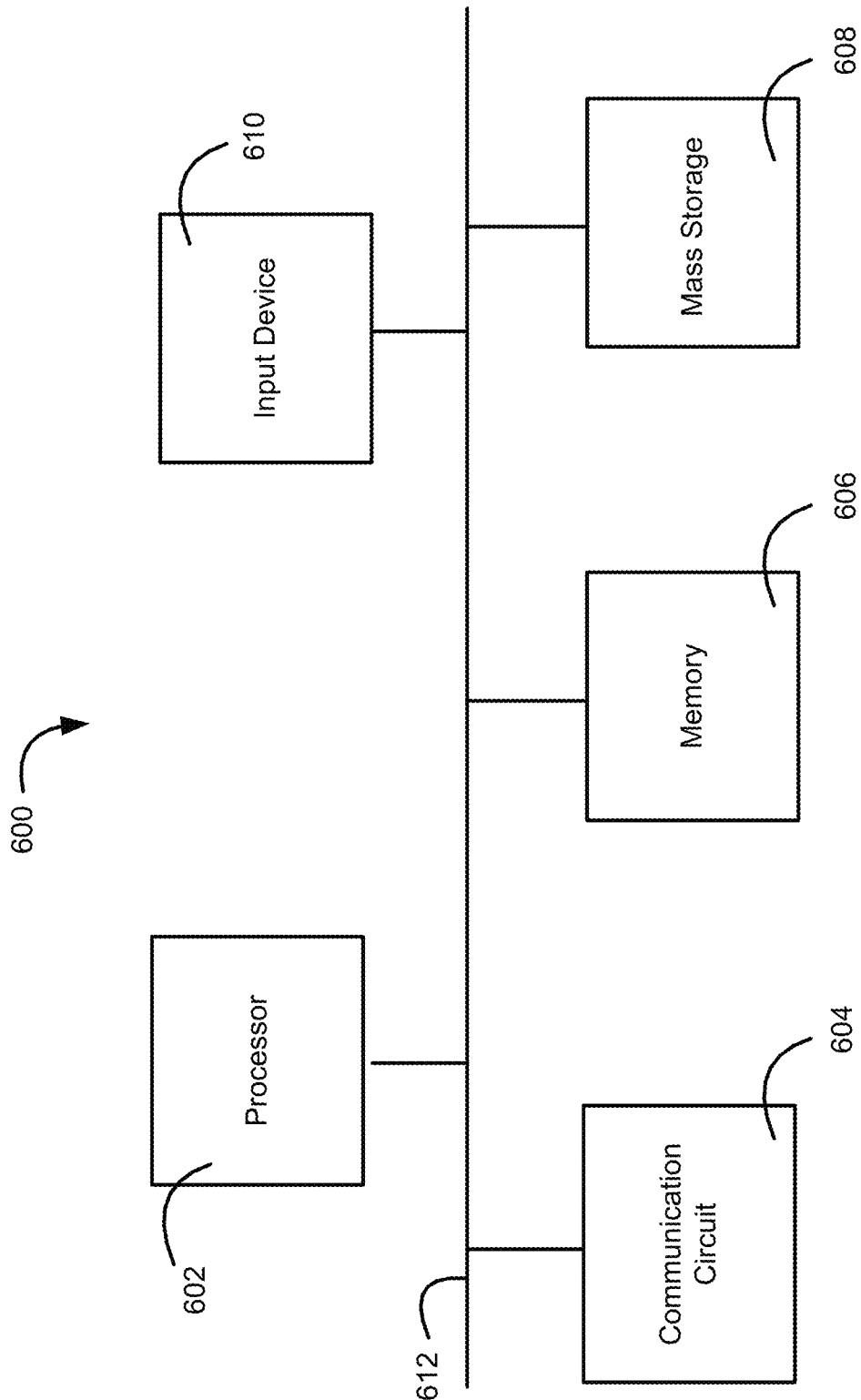
FIG. 6 is a block diagram illustrating example components of an apparatus that may be configured to perform the tasks described in one or more embodiments provided herein.

The systems, methods, and/or instrumentalities described herein may be implemented using one or more processors, one or more storage devices, and/or other suitable accessory devices such as display devices, communication devices, input/output devices, etc. FIG. 6 is a block diagram illustrating an example apparatus 600 that may be configured to automatically determine the shape and/or location of an organ in accordance with one or more embodiments described herein. As shown, the apparatus 600 may include a processor (e.g., one or more processors) 602, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The apparatus 600 may further include a communication circuit 604, a memory 606, a mass storage device 608, an input device 610, and/or a communication link 612 (e.g., a communication bus) over which the one or more components shown in the figure may exchange information.

The communication circuit 604 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 606 may include a storage medium (e.g., a non-transitory storage medium) configured to store machine-readable instructions that, when executed, cause the processor 602 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 608 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 602. The input device 610 may include a keyboard, a mouse, a voice-controlled input device, a touch sensitive input device (e.g., a touch screen), and/or the like for receiving user inputs to the apparatus 600.

It should be noted that the apparatus 600 may operate as a standalone device or may be connected (e.g., networked or clustered) with other computation devices to perform the functions described herein. And even though only one instance of each component is shown in FIG. 6, a skilled person in the art will understand that the apparatus 600 may include multiple instances of one or more of the components shown in the figure.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. An apparatus, comprising:
one or more processors configured to:
obtain a first model of a patient, wherein the first model indicates a body shape or a pose of the patient;
obtain a representation of an organ of the patient, wherein the representation indicates a geometric characteristic of the organ corresponding to the body shape or the pose of the patient indicated by the first model;
determine, using an artificial neural network (ANN), a relationship between the geometric characteristic of the organ and the body shape or the pose of the patient, wherein the relationship is determined by the ANN based on the first model of the patient and the representation of the organ;
obtain a second model of the patient, wherein the second model indicates that at least one of the body shape or the pose of the patient has changed in the second model compared to the first model; and
determine, based on the second model and the relationship between the geometric characteristic of the organ and the body shape or the pose of the patient determined by the ANN, the geometric characteristic of the organ that corresponds to the body shape or the pose of the patient indicated by the second model.

2. The apparatus of claim 1, wherein the geometric characteristic of the organ includes at least one of a shape of the organ or a location of the organ.

3. The apparatus of claim 1, wherein the representation of the organ comprises a point cloud associated with the organ.

4. The apparatus of claim 3, wherein the point cloud is obtained based on a scan image of the patient taken while the patient is in the body shape or the pose indicated by the first model.

5. The apparatus of claim 1, wherein the one or more processors being configured to determine the relationship between the geometric characteristic of the organ and the body shape or the pose of the patient comprises the one or more processors being configured to determine a plurality of parameters that indicates a spatial relationship between one or more points of the organ in an image space and one or more points of the first model in the image space.

6. The apparatus of claim 5, wherein the ANN is trained to determine the relationship between the geometric characteristic of the organ and the body shape or the pose of the patient based on a plurality of patient training models and a plurality of training representations of the organ, and wherein, during the training, the ANN is configured to:
obtain a first patient training model from the plurality of patient training models;
obtain a first training representation of the organ from the plurality of training representations, wherein the first training representation indicates the geometric characteristic of the organ that corresponds to a first patient body shape or a first patient pose indicated by the first patient training model;
estimate values of the plurality of parameters based on the first patient training model and the first training representation of the organ;
obtain a second patient training model from the plurality of patient training models;
obtain a second training representation of the organ from the plurality of training representations as a ground truth representation of the organ, wherein the second training representation of the organ indicates the geometric characteristic of the organ that corresponds to a second patient body shape or a second patient pose indicated by the second patient training model;
predict a representation of the organ based on the estimated values of the plurality of parameters and the second patient training model; and
adjust operating parameters of the ANN based on a difference between the predicted representation of the organ and the ground truth representation of the organ.

7. The apparatus of claim 1, wherein the ANN comprises one or more encoders and one or more decoders, the one or more encoders configured to determine the relationship between the geometric characteristic of the organ and the body shape or the pose of the patient, the one or more decoders configured to generate, based on the second model of the patient and the relationship determined by the one or more encoders, an estimated representation of the organ corresponding to the body shape or the pose of the patient indicated by the second model.

8. The apparatus of claim 1, wherein at least one of the first model or the second model of the patient comprises a parametric model of the patient.

9. The apparatus of claim 1, wherein the one or more processors being configured to obtain the first model of the patient comprises the one or more processors being configured to construct the first model based on a first image of the patient, and wherein the one or more processors being configured to obtain the second model of the patient comprises the one or more processors being configured to construct the second model based on a second image of the patient.

10. The apparatus of claim 9, further comprising a sensing device configured to capture the first image of the patient and the second image of the patient.

11. The apparatus of claim 1, wherein the one or more processors are further configured to align the representation of the organ with the second model of the patient based on the geometric characteristic of the organ that corresponds to the body shape or the pose of the patient indicated by the second model.

12. A method, comprising:
obtaining a first model of a patient, wherein the first model indicates a body shape or a pose of the patient;
obtaining a representation of an organ of the patient, wherein the representation indicates a geometric characteristic of the organ corresponding to the body shape or the pose of the patient indicated by the first model;
determining, using an artificial neural network (ANN), a relationship between the geometric characteristic of the organ and the body shape or the pose of the patient, wherein the relationship is determined by the ANN based on the first model of the patient and the representation of the organ;
obtaining a second model of the patient, wherein the second model indicates that at least one of the body shape or the pose of the patient has changed in the second model compared to the first model; and
determining, based on the second model and the relationship between the geometric characteristic of the organ and the body shape or the pose of the patient determined by the ANN, the geometric characteristic of the organ that corresponds to the body shape or the pose of the patient indicated by the second model.

13. The method of claim 12, wherein the geometric characteristic of the organ includes at least one of a shape of the organ or a location of the organ.

14. The method of claim 12, wherein the representation of the organ comprises a point cloud associated with the organ, and wherein the point cloud is obtained based on a scan image of the patient taken while the patient is in the body shape or the pose indicated by the first model.

15. The method of claim 12, wherein determining the relationship between the geometric characteristic of the organ and the body shape or the pose of the patient comprises determining a plurality of parameters that indicates a spatial relationship between one or more points of the organ in an image space and one or more points of the first model in the image space.

16. The method of claim 15, wherein the ANN is trained to determine the relationship between the geometric characteristic of the organ and the body shape or the pose of the patient based on a plurality of patient training models and a plurality of training representations of the organ, and wherein, during the training, the ANN is configured to:
obtain a first patient training model from the plurality of patient training models;
obtain a first training representation of the organ from the plurality of training representations, wherein the first training representation indicates the geometric characteristic of the organ that corresponds to a first patient body shape or a first patient pose indicated by the first patient training model;
estimate values of the plurality of parameters based on the first patient training model and the first training representation of the organ;
obtain a second patient training model from the plurality of patient training models;
obtain a second training representation of the organ from the plurality of training representations as a ground truth representation of the organ, wherein the second training representation of the organ indicates the geometric characteristic of the organ that corresponds to a second patient body shape or a second patient pose indicated by the second patient training model;
predict a representation of the organ based on the estimated values of the plurality of parameters and the second patient training model; and
adjust operating parameters of the ANN based on a difference between the predicted representation of the organ and the ground truth representation of the organ.

17. The method of claim 12, wherein at least one of the first model or the second model of the patient comprises a parametric model of the patient.

18. The method of claim 12, wherein obtaining the first model of the patient comprises constructing the first model based on a first image of the patient and wherein obtaining the second model of the patient comprises constructing the second model based on a second image of the patient.

19. The method of claim 18, further comprising capturing, via a sensing device, the first image of the patient and the second image of the patient.

20. The method of claim 12, further comprising aligning the representation of the organ with the second model of the patient based on the geometric characteristic of the organ that corresponds to the body shape or the pose of the patient indicated by the second model.

* * * * *